United States Patent [19]

Tamm et al.

[11] Patent Number: 5,005,976
[45] Date of Patent: Apr. 9, 1991

[54] ELECTROTHERMAL ATOMIZATION OF A SAMPLE FOR SPECTROSCOPIC PURPOSES

[76] Inventors: Rolf Tamm, Am Fohrenbuhl 8, 7777 Salem 2; Bernhard Huber, Hildegardring 42, 7770 Überlingen; Gunther Rodel, Hinter den Garten 13, 7776 Owingen; Erich Stengele, Dorfstr. 23, 7776 Taisersdorf, all of Fed. Rep. of Germany

[21] Appl. No.: 377,992

[22] Filed: Jul. 11, 1989

[30] Foreign Application Priority Data

Jul. 13, 1988 [DE] Fed. Rep. of Germany ....... 3823733

[51] Int. Cl.$^5$ .......................... G01J 3/30; G01N 21/74
[52] U.S. Cl. ...................................... 356/312; 356/244
[58] Field of Search .................. 356/312, 244

[56] References Cited

U.S. PATENT DOCUMENTS

| | | | |
|---|---|---|---|
| 4,022,530 | 5/1977 | Braun et al. | 356/312 |
| 4,098,554 | 7/1978 | Huber et al. | 356/312 |
| 4,660,976 | 4/1987 | Falk | 356/312 |
| 4,681,536 | 7/1987 | Jansen | 432/59 |
| 4,834,536 | 5/1989 | Tamm et al. | 356/312 |

Primary Examiner—F. L. Evans
Assistant Examiner—K. P. Hantis
Attorney, Agent, or Firm—Thomas P. Murphy; Edwin T. Grimes

[57] ABSTRACT

A device for electrothermal atomization of a sample for spectroscopic purposes comprises a furnace (10) which is held between two contacts (54, 56). The contacts (54, 56) surround the furnace (10) and form a cavity (58) with an insulating gap (88) being formed between the contacts (54, 56). This gap (88) is closed by a seal (142) made of ceramic felt so that inert gas passed into the cavity (58) emerges only through a bore (14) of the furnace (10) and sample inlet ports (116, 120). Thereby, the inert gas consumption is reduced well-defined flow conditions also result for the inert gas in the cavity (58) which expands when the furnace (10) is heated.

29 Claims, 2 Drawing Sheets

ELECTROTHERMAL ATOMIZATION OF A SAMPLE FOR SPECTROSCOPIC PURPOSES

BACKGROUND AND SUMMARY OF THE INVENTION

The present invention relates to spectroscopy and more particularly a device for electrothermal atomization of a sample for spectroscopic analysis.

Electrothermal atomizers, commonly referred to as heated graphite atomizers or graphite furnaces, are utilized in atomic absorption spectrophotometers for rendering the sample to be analyzed in atomic form. Typically, the furnaces comprise a tubular graphite member clamped between annular graphite contacts or electrodes engaging its respective ends. A lateral opening in the side wall of the graphite tube serves as a sample port accommodating the insertion of the substance to be analyzed into the tubular member.

The graphite contacts, usually mounted in cooling jackets, are pressed into tight engagement with the ends of the tubular furnace member by resilient biasing means or a servomotor. An intense electrical current, passed longitudinally through the tubular member between the contacts, heats the member to the high temperature required to convert the sample to a "cloud of atoms". The sample is thereby atomized such that an atomic cloud is generated within the graphite tube.

A measuring light beam of a line emitting light source which comprises the resonant spectral line of a looked-for element is passed through the annular graphite contacts and the longitudinal bore of the graphite tube. The amount of the looked-for element in the sample can be determined from the absorption of the measuring light beam.

In order to prevent rapid deterioration of the tubular graphite member by oxidation at the high temperatures required for atomization of the analyte, provision is made for enveloping it in a flow of inert protective gas. The graphite tube is surrounded by an inert gas such that oxygen does not come into contact with the graphite tube.

A graphite furnace of the type just described is shown in Braun et al., U.S. Pat. No. 4,022,530 which is incorporated herein by reference. In this particular furnace, the contacts are tubular. The two contacts extend around the graphite tube along its entire length between the contact surfaces except for a separating gap. An inert gas flow is passed into the graphite tube from both ends. This inert gas flow emerges through a radial bore of the graphite tube in its center. One of the tubular contacts has a radial bore which is aligned with the radial bore of the graphite tube.

The contacts of the contact arrangement form a cavity wherein the graphite tube is held. Inert gas is introduced into this cavity and flows around the graphite tube. Two inert gas flows are thereby generated, one of which flows through the interior of the graphite tube, usually from the ends of the graphite tube inward and then exhausting through the central lateral opening (i.e., sample inlet port) and the other which flows around the outside of the graphite tube. A portion of the latter inert gas flow emerges through the gap which is necessarily formed between the two electrodes which have to be electrically insulated from each other. Thus, the passage of oxygen through the gap into the cavity and to the graphite tube is prevented. This gap causes quite a high consumption of inert gas. Additionally, disturbances occur whereby thermal decomposition products of the sample are guided over areas of relatively low temperature.

In Hutsch et al., U.S. Pat. 4,726,678 which is incorporated herein by reference and the publication in "Analytical Chemistry" 58 (1986), 1973, a graphite furnace is described in which the tubular furnace body has a rectangular cross-section and contact projections extend transversely to the axis of the furnace body. The furnace body and contact projections are formed as one integral graphite element. Current for heating the furnace is supplied through contact projections tranverse to the longitudinal axis of the tubular furnace body.

It is an object of the present invention to provide a new and improved electrothermal atomization furnace assembly which is particularly advantageous in atomic absorption spectroscopy.

Another object of the invention is to provide an electrothermal atomization furnace assembly which reduces the consumption of inert gas.

A further object of the invention is to provide such a furnace assembly which achieves a well-defined inert gas flow for effective protection of the furnace body against exposure to atmospheric oxygen and which prevents precipitation of sample components at relatively cold areas of the furnace assembly.

A further object of the invention is to provide such a furnace assembly which permits selective relative adjustment of inert gas flow over and within the furnace body.

Other objects will be in part obvious and in part pointed out more in detail hereinafter.

Accordingly, it has been found that the foregoing and related objects are attained in an electrothermal atomization furnace assembly having an electrothermal furnace body with contact surfaces configured for mounting engagement between coacting electrical contacts, a bore adapted for passing a measuring light beam therethrough and a sample port for introducing sample into the bore and exhausting inert gas flow and sample components therefrom. A pair of current-supplying contacts operationally mount the furnace body therebetween and are configured to form a cavity containing said furnace body and have a through-bore in alignment with the sample port. The contacts are in non-conductive spaced disposition so as to form a predetermined gap therebetween. Inert gas passageways in the contacts provide inert gas flow into the cavity for defined flow about and within the furnace body to prevent exposure to oxygen and remove sample components. An electrically insulating seal is mounted in said gap for sealing against inert gas loss from the cavity.

The furnace is arranged in a cavity which is closed except for the though-bore aligned with the sample inlet port. From this closed cavity the inert gas flow can only emerge through the through-bore. Thus, the discharge of gas through an additional gap is prevented which results in a considerable economizing of inert gas and which also prevents flows which flow to such a gap. It has been found that such sealing of the gap between the contacts can be realized in practice despite the extremely high temperatures to which the furnace is heated in operation.

Advantageously the contacts are held in cooling jackets. Therefore, the contacts themselves, between which the seal is arranged, are relatively cold compared to the furnace itself. The seal is substantially shielded from the furnace by the cooled contacts. In this way, unacceptable heating of the seal by the radiation of the glowing furnace is counteracted.

DESCRIPTION OF THE PREFERRED EMBODIMENT

Figure 1:
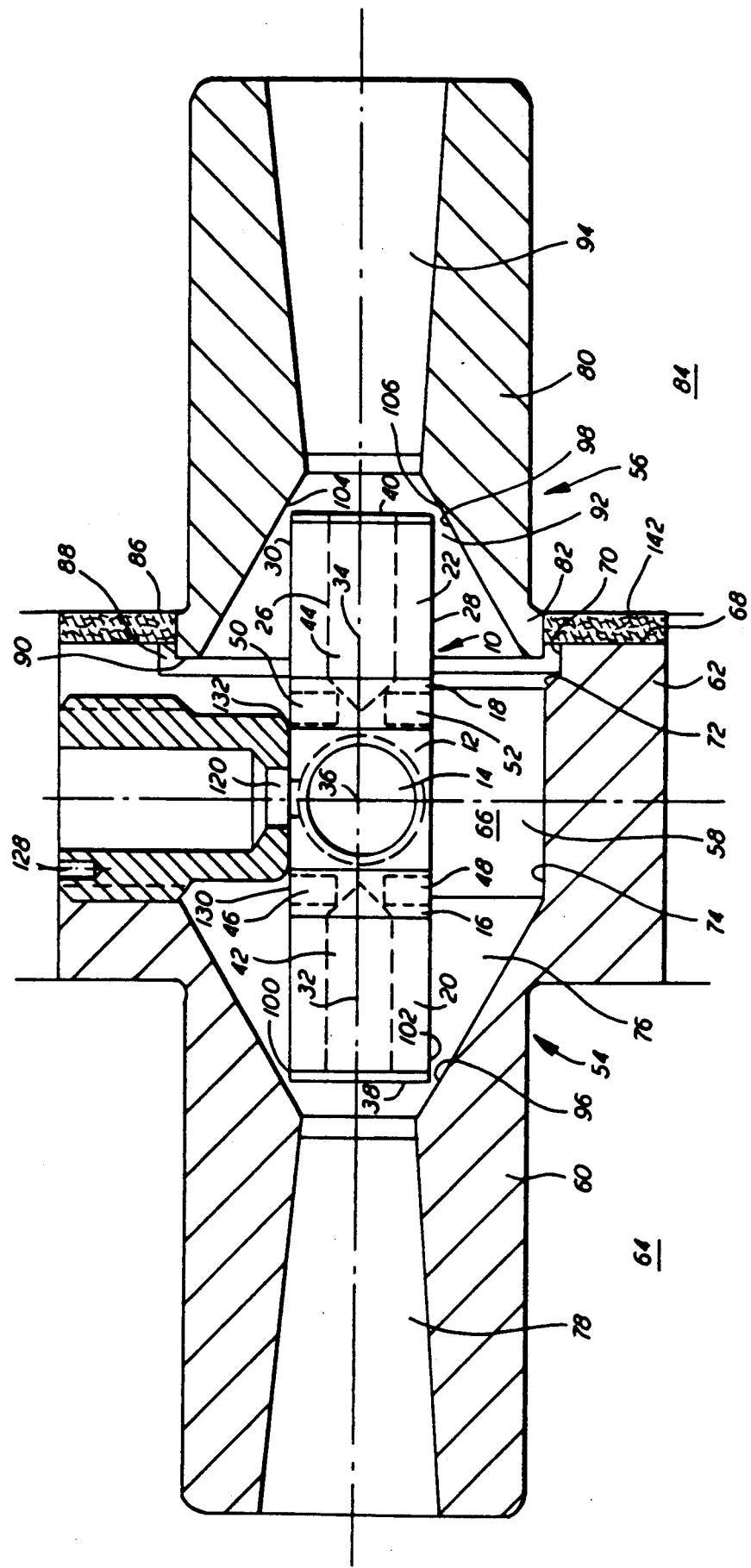
FIG. 1 is a sectional view of the device of the present invention for electrothermal atomization of a sample with a furnace and two contacts which form a closed cavity for the furnace.

Although specific forms of the present invention have been selected for illustration in the drawings, and the following description is drawn in specific terms for the purpose of describing these forms of the invention, the description is not intended to limit the scope of the invention which is defined in the appended claims.

Referring to FIG. 1, the numeral 10 generally designates a furnace for electrothermal atomization of a sample. The furnace 10 is made of graphite and has a substantially tubular furnace body 12 with a bore 14 extending therethrough. Contact webs 16 and 18 extend along the furnace body 12 on opposite sides. In plan view (from the top as shown in FIG. 1), the contact webs are trapezoidal shape with the longer parallel side of the trapezoid being integral with the furnace body 12.

Contact elements 20 and 22, respectively, are provided at the contact webs 16 and 18. The contact elements 20 and 22 are generally cylindrical with opposite cylindrical outer surface portions 24 and 26 (FIG. 2) and opposite parallel planar surfaces 28 and 30. The axes 32 and 34 of the contact elements 20 and 22, respectively, extend perpendicular to the axis 36 of the bore 14. Conically tapering portions are provided as contact surfaces 38 and 40, respectively, at the ends of the contact elements 20 and 22 in the area of the cylindrical outer surfaces 24, 26 shown n FIG. 2. As illustrated in FIG. 1 in broken line, axial inert gas passages 42 and 44, respectively, are provided in the contact elements 20 and 22. The inert gas passages 42 and 44 intersect cutouts 46, 48 and 50, 52, respectively, which are provided along the furnace body 12 on the upper side and on the lower side of the contact webs 16 and 18, respectively.

Figure 4:
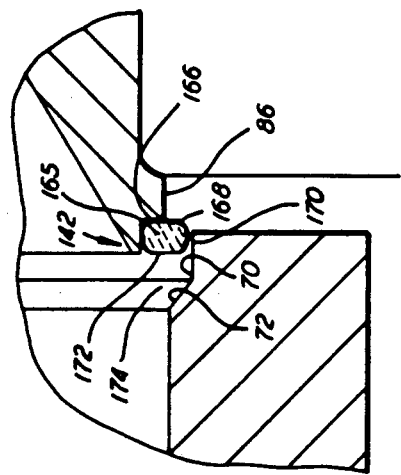
FIG. 4 is an enlarged sectional view of a further embodiment of the seal in an assembly similar to FIG. 1.

The furnace is constructed substantially as the furnace according to FIGS. 4–6 of the commonly owned, copending U.S. Pat. Application S.N. 304,9933, filed February 1, 1989 and incorporated herein by reference.

The furnace 10 is held between a first contact 54 and a second contact 56 by resilient biasing means or a servomotor (not shown). Current is passed through the furnace 10 via the contacts 54 and 56. The contacts 54 and 56 are also made of graphite form a cavity 58 which accommodates the furnace 10.

The first contact 54 has a shaft 60 and a head 62. The contact 54 is held in a cooling device or jacket 64 with the shaft 60. The contact 54 has a central cutout 66 which originates from the end face 68 of the head 62. This cutout 66 comprises a flat-cylindrical section 70 which communicates with a conical shoulder 72. A cylindrical section 74 is formed adjacent to the shoulder 72. The section 74 communicates with a conical section 76. An inert gas passage 78 extends along the shaft 60 and ends in the conical section 76.

The second contact 56 has also a shaft 80 and a head 82. The shaft 80 is arranged in a cooling device or jacket 84. The head 82 is relatively short in its axial direction with an outer diameter smaller than the inner diameter of the section 70 of the cutout 66 in the contact 54. The head 82 of the contact 56 projects into the section 70 of the cutout 66 of the contact 54. A rather wide gap 88 is formed between the wall of the section 70 and the outer surface 86 of the head 82. A conical cutout 92 is formed in the end face 90 of the head 82. An inert gas supply passage 94 extends centrally along the shaft 80 and ends in the cutout 92.

The conical section 76 of the cutout 66 forms a conical contact surface 96 on the first contact 54. The conical cutout 92 forms a conical contact surface 98 on the second contact 56. The furnace 10 with its complementary conical contact surfaces 38 and 40 is held between these two conical contact surfaces 96 and 98. The furnace is held in front of and behind the plane of the paper of FIG. 1 because of the planar surfaces 28, 30.

Inert gas ports 100, 102 and 104, 106, respectively, are provided between the contact surfaces 96 and 98 and the planar surfaces 28 and 30. In operation, inert gas emerges from the inert gas supply passages 78 and 94 through the inert gas inlet ports 100, 102, 104 and 106 into the cavity 58. Inert gas also flows through the inert gas passages 42 and 44 and the interconnected cutouts 46, 48, 50 and 52 into the cavity 58.

Figure 2:
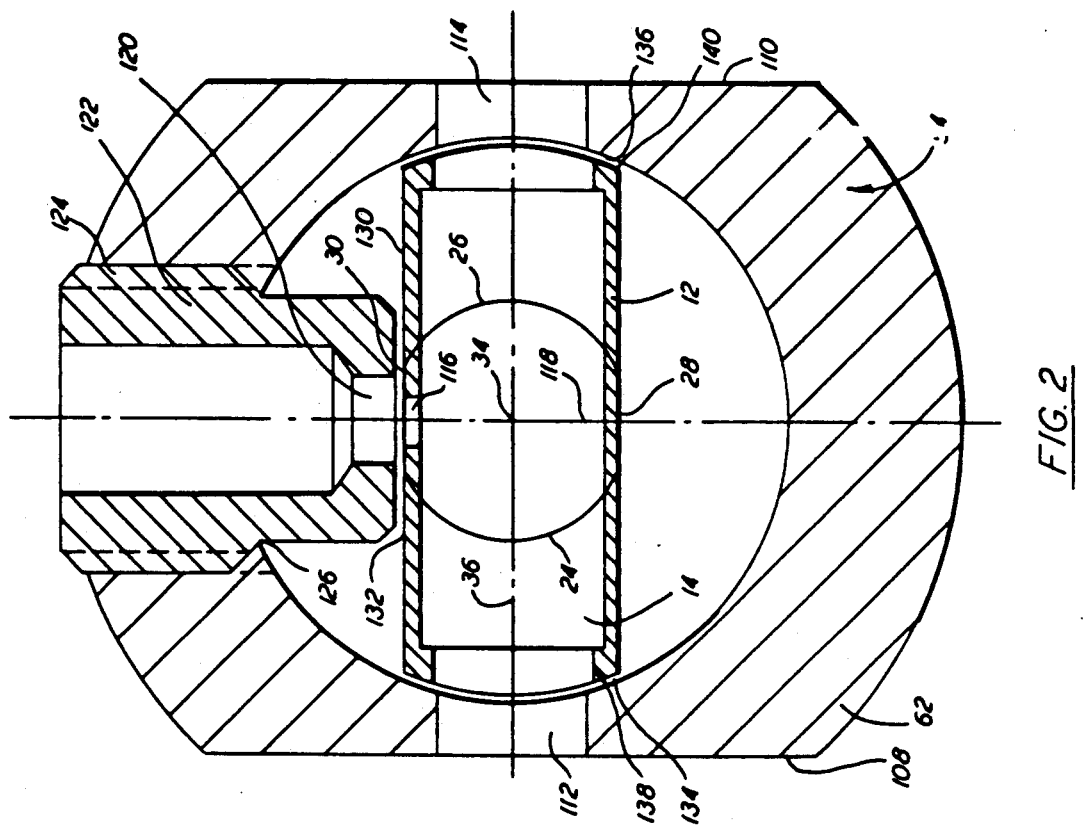
FIG. 2 is a sectional view taken along line II—II of FIG. 1.

As can best be seen in FIG. 2, the head 62 of the contact 54 has parallel planar surfaces 108 and 110. Aligned apertures 112 and 114, respectively, are provided in the area of these planar surfaces 108 and 110 and end in the cylindrical section 74 of the cutout 66. In operational assembly, these apertures 112 and 114 are aligned with the bore 14 of the furnace body 12 and a measuring light beam can pass along the axis 36 of the bore 14 of the furnace body 12 through the aperture 112, the bore 14 and the aperture 114. In an atomic absorption spectrophotometer, the apertures 112 and 114 are closed from atmosphere by windows in a conventional manner which need not be illustrated in detail.

The furnace body 12 has a central lateral sample inlet port 116. In operational assembly, the axis 118 of the sample inlet port 116 is parallel to the planar surfaces 108 and 110 of head 62 and perpendicular to the axis 34 of contact element 22 and axis 36 of bore 14.

A sample inlet port or through-bore 120 in the contact 54 is aligned with the sample inlet port 116 of the furnace body 12. The sample inlet port 120 of the contact 54 is formed by an axially adjustable chimney 122. The chimney 122 is axially adjustable by means of an outer thread 124 in a threaded bore 126 of the contact 54. A blind eccentric bore 128 in the outer end face of the chimney 122 permits engagement with a suitable tool and rotation of the chimney 122 for axial adjustment thereof.

The furnace 10 forms a planar surface 130 which includes the planar surface 30 of contact elements 20, 22. An annular gap 132 is formed between the inner end face of the chimney 122 and the planar surface 130. The width of this annular gap 132 is varied by axial adjustment of the chimney. Annular gaps 134 and 136 (FIG. 2) are formed between the cylindrical end faces 138 and 140 of the furnace body 12 and the inner wall of section 74 of the cutout 66.

The cavity 58 is closed by a seal 142 which extends beyond the gap 88 between the contacts 54 and 56. The seal 142 is an annular disc made of a ceramic felt (ceramic fiber reinforced alumina composition, type 100, A 1203/SiO2. The seal 142 is mounted at the outer surface 86 of the head 82 of the contact 56 and is supported by the cooling jacket 84. In operational assembly, the seal 142 engages the end face 68 of the head 62 of the contact 54. Thus, the seal is in contact with the cooling device 84 and with the cooled contacts 54 and 56. As far as possible, the seal is shielded by the contacts 54 and 56 from the heat radiation of the glowing furnace body 12 during atomization. It has been found that under these circumstances, the seal 142 is not affected by the heating of the furnace body 12.

The seal 142 sufficiently closes the gap 88 such that virtually no inert gas flow passes though the gap 88. On the other hand, the seal also effects electric insulation between the two contacts 54 and 56. The elasticity of the ceramic felt accommodates the thermal dilatation of the elements. At the same time, the seal ensures that in case of breaking of the furnace 10, the contacts 54 and 56 will not come into contact with each other and thus cannot effect a short circuit.

In the assembly described, the inert gas flows from the inner gas inlet ports 100, 102, 104 and 106 inward to the furnace body 12. Then, a partial flow passes over the outside of the furnace body 12 through the annular gaps 134 and 136 and from there, inwardly along the bore 14 to the sample inlet port 116. This inert gas emerges through the sample inlet port 116 and the chimney 122. This inert gas flow will also remove thermal decomposition products of the sample. As indicated in FIG. 2 by arrows, a further partial flow of inert gas passes through the annular gap 132 directly to the chimney 122. The ratio of these different partial flows can be selectively varied by adjustment of the width of the annular gap 132 through vertical adjustment of the chimney.

As described, there is no flow through the gap 88. Since the gap 88 has to be quite wide in order to ensure safe electric insulation between the contacts 54 and 56, a considerable inert gas flow through this gap would occur in prior art arrangements of the present type without a seal 142. Without seal 142, such an inert gas flow would also be necessary in order to avoid the access of oxygen. The necessity of this inert gas flow is avoided by use of the seal 142 and thus, economizing of inert gas results. Furthermore, such a strong inert gas flow through the gap 88 as would occur without seal 142 would considerably disturb the inert gas flow within the cavity 58. By sealing the gap 88 with the seal 142, a well-defined flow is attained within the cavity 58 as described above.

For atomization of sample, the furnace body 12 is heated to a very high temperature, e.g., more than 1000°. The sample introduced through the sample inlet ports 120 and 116 is atomized in the bore 14. The atomic vapor is thus generated in the bore 14 wherein the components of the sample are present in atomic state. A measuring light beam which originates from a light source specifically emitting the resonant lines of a looked-for element passes through this atomic vapor along the axis 36 and is absorbed according to the proportion of this looked-for element in the sample.

During this procedure, the inert gas supply is interrupted for a short period to ensure that the atomic vapor remains in the path of rays of the measuring light beam as long as possible for the measurement and is not immediately flushed out of the bore by the inert gas flow. By heating the furnace body 12, the inert gas volume within the cavity including the bore is also heated and its volume is increased to a multiple thereof. Thus, because of this heating, an inert gas flow is generated. Without the seal, this inert gas flow caused by the heating would emerge predominantly through the gap 88. This would result in very complex flow conditions and could result in sample vapor being conveyed to relatively cold portions with precipitation thereon.

The furnace assembly of the present invention has been described herein for use in atomic absorption spectroscopy. However, the invention can be utilized for other procedures in which an atomization of sample is effected for spectroscopic purposes. For example, the invention may also be utilized in procedure in which an atomization is effected in an inert gas atmosphere and a gas discharge is generated which permits simultaneous observation of the emission lines of several elements contained in the sample.

Figure 3:
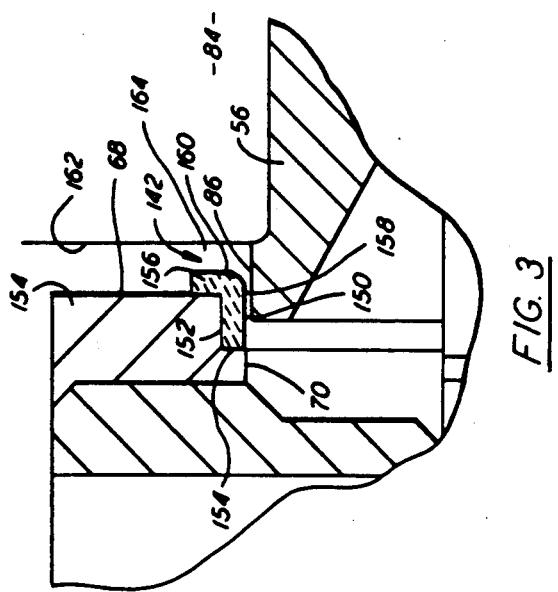
FIG. 3 is an enlarged sectional view of another embodiment of the seal in an assembly similar to FIG. 1.

In the embodiment according to FIG. 3, a ceramic ring seal 150 is mounted in the contact 54. The ceramic ring 150 has a substantially L-shaped cross-section and comprises a sleeve-shaped portion 152 and an annular disk element 156. The sleeve-shaped portion 152 is inserted in a recess 154 at the inner surface 70 of the cutout 66 and the annular disc element 156 extends outwardly in front of the end face 68 of the contact 54. The sleeve-shaped portion 152 forms with the outer surface 86 of the contact 56 a well-defined, narrow gap 158 of 0,075 mm, for example. A small inert gas flow can pass through this gap 158 which may correspond approximately to the inert gas flow which passes through a seal made of ceramic felt. However, such an inert gas flow is negligible and is substantially smaller than the inert gas flow which would pass through the gap 88 between the contacts (FIG. 1) absent the seal. Since the gap 158 is limited on one side by an insulating ceramic portion, namely the ceramic ring 150, the gap 158 can be very narrow without the risk of contact and thus short circuit between the two contacts 54 and 56. Since the gap 158 is a circumferential gap, it virtually does not change when the contacts 54 and 56 thermally dilitate when the furnace is heated.

The end face 160 of the annular disc element 156 is spaced by a predetermined distance from the opposite end face 162 of the cooling device 84 such that the gap 164 formed therebetween is able to accommodate the thermal dilatation of the contacts 54 and 56. The insulating annular disc element 156 also ensures that no direct contact between the end faces 68 and 162 of the contact 54 and the cooling device 84, respectively, will be established with thermal dilatation. Thus, the annular disc element 156 also represents a short circuit safety device.

In the embodiment according to FIG. 4, a ceramic ring seal 165 having a substantially square or rectangular cross-section is inserted into a recess 166 of the contact 56. The cylindrical outer surface 168 of the ceramic ring 165 forms a narrow gap 170 with the cylindrical section 70 of the cutout 66 of the contact 54. Again, this gap is substantially narrower than the gap 88 (FIG. 1) between the contacts themselves which is made possible by the insulating characteristics of the ceramic ring 165. Under ambient or cold conditions of the contacts, the end face 172 of the ceramic ring 165 is spaced from the ring shoulder 72 at such distance that the gap 174 formed therebetween is able to accommodate thermal dilatation of the contacts 54 and 56. The ceramic ring 165 also operates as a short circuit safety device in the axial direction because of thermal dilatation or position tolerances since the insulating ceramic ring 165 would engage the ring shoulder 72.

Accordingly, as can be seen, an electrothermal atomization furnace assembly has been described which reduces the consumption of inert gas and achieves a well-defined inert gas flow for effective furnace protection and avoidance of undesirable precipitation. Furthermore, selective relative adjustment of inert gas flow over and within the graphite tube is attained.

As will be apparent to persons skilled in the art, various modifications and adaptations of the structure above described will become readily apparent without departure from the spirit and scope of the invention, the scope of which is defined in the appended claims.

What is claimed is:

1. An electrothermal atomization furnace assembly comprising
an electrothermal furnace body having a furnace bore adapted for passing a radiation beam therethrough, a sample port for introducing sample into the furnace bore and contact surfaces configured for mounting engagement between coacting electrical contacts for supplying electrical current through said furnace body,
current-supplying contact means for operationally mounting the furnace body and supplying current therethrough to heat the furnace body for sample atomization,
said contact means comprising first and second contact elements coacting to form a cavity containing said furnace body and having a though-bore in alignment with said sample port for introducing sample into the furnace body and exhausting inert gas and sample components, said first and second contact elements being in non-contacting disposition to form a predetermined gap therebetween,
electrically insulating seal means for sealing said gap against inert gas loss from said cavity, and
said contact means having means for providing inert gas in a defined flow about and within said furnace body to prevent exposure to oxygen and exhausting out said throughbore.

2. The assembly of claim 1 comprising
first and second cooling jackets enveloping said first and second contact elements respectively and
said first and second contact elements being configured to substantially shield said seal means from heat radiation from said furnace body.

3. The assembly of claim 2 wherein said seal means comprises a ceramic felt seal.

4. The assembly of claim 3 wherein said seal engages one of said first and second cooling jackets.

5. The assembly of claim 1 wherein said seal means comprises a ceramic felt seal.

6. The assembly of claim 1 wherein said seal means comprises an annular seal mounted in engagement with said first and second contact elements so as to close off said gap.

7. The assembly of claim 6 wherein said seal is sufficiently elastic to accommodate thermal dilatation of said first and second contact elements during atomization operation.

8. The assembly of claim 1 wherein said seal means comprises an annular seal mounted to said first contact element in spaced disposition to said second contact element to form a predetermined narrow interstice.

9. The assembly of claim 8 wherein said annular seal has an outer surface and said second contact element has an outer wall portion, said narrow interstice being formed between said outer surface and said outer wall portion.

10. The assembly of claim 9 wherein said first and second contact elements and said seal are configured and disposed to accommodate thermal dilatation of said first and second contact elements during heating.

11. The assembly of claim 9 wherein said seal has an L-shape cross-section.

12. The assembly of claim 9 wherein said seal has a rectangular cross-section.

13. The assembly of claim 1 wherein
said means for providing inert gas comprises gas supply passageways for conducting inert gas into said cavity and said cavity being configured so as to direct inert gas flowing into said cavity in a defined flow about said furnace body and a defined flow through said furnace body with said flows discharging out said through-bore.

14. The assembly of claim 13 wherein said furnace body comprises gas passageways for directing inert gas flow in said cavity.

15. The assembly of claim 13 wherein a chimney element is mounted in said through-bore for conducting sample into the furnace body and exhausting inert gas and sample components, said chimney element having an interior end in spaced disposition from said sample port of said furnace body to form an inlet gap to said chimney element so as to permit inert gas flow about said furnace body to exhaust through said chimney element.

16. The assembly of claim 15 which comprises means for selectively adjusting the spaced disposition of said chimney element to vary the size of said inlet gap to regulate the flow of inert gas therethrough.

17. A device for electrothermal atomization of sample for spectroscopic analysis comprising (a) a furnace (10) having contact surfaces (38, 40) for supplying electric current through the furnace (10) for heating and a bore (14) configured for passing a measuring light beam, (b) a pair of current-supplying electric contacts (54, 56), mounting the furnace at its contact surfaces (38, 40), said contacts (54, 56) surrounding the furnace (10) to form a cavity (58) containing the furnace (10) and a gap (88) between said contacts (54, 56), (c) an electrically insulating seal (142) mounted in said gap (88) for sealing against inert gas loss from said cavity (58), (d) aligned sample inlet ports (116, 120) in the furnace (10) and in one of the contacts (54) for introducing sample into the bore (14) of the furnace (10), (e) apertures (112, 114) in the contacts (54, 56) aligned with the bore (14) of the furnace (10), said apertures (112, 114) being sealed by windows which permit passage of the measuring light beam, and (f) means for guiding an inert gas flow over inner and outer surfaces of the furnace (10) to prevent access of air oxygen to the furnace (10) and for the removal of the sample components.

18. The device of claim 17 wherein said contacts (54, 56) are mounted in cooling jackets (64, 84).

19. The device of claim 18 wherein said contacts (54, 56) and said seal (142) are relatively disposed so that the seal (142) is substantially shielded from the furnace (10) by the cooled contacts (54, 56).

20. The device of claim 19 wherein the seal (142) is formed by a ceramic felt.

21. The device of claim 17 wherein the seal is a ceramic ring arranged at one of the contacts so as to form a narrow gap with the other contact.

22. The device of claim 21 wherein the ceramic ring has an outer surface and said other contact has a cylindrical inner wall portion and said narrow gap is formed between said outer surface of the ceramic ring and said cylindrical inner wall portion of said other contact.

23. The device of claim 22 wherein said ceramic ring has an end face spaced from said other contact to form an interspace sufficient to accommodate longitudinal dilatation of the contacts upon heating of the furnace (10).

24. The device of claim 23 wherein the ceramic ring (150) has an L-shaped cross-section with a sleeve-shaped portion (152) held in a recess (154) of an inner surface (70) of a cutout (66) of the one contact (54) and an annular disc element (156) extending beyond the end face (68) of the contact (54), said narrow gap (158) being formed circumferentially between the inner surface of the sleeve-shaped portion (152) and an outer surface (86) of the other contact (56) projecting into the cutout (66) of said one contact (54) and the end face (160) of the annular disc element (156) being spaced from an opposite end face (162) in conductive connection with the other contact (56).

25. The device of claim 23 wherein said other contact (54) has a cutout (66) with a cylindrical section (70), said ceramic ring (165) being mounted to said one contact (56) and disposed within said cutout (66), said ceramic ring having an outer surface (168) projecting beyond the outer surface (86) of said one contact (56) to define a narrow circumferential gap (170) between said cylindrical section (70) of said other contact (54) and said outer surface (168).

26. The device of claim 17 wherein
    (a) the furnace (10) has a substantially tubular furnace body (12) forming said bore (14) for the passage of the measuring light beam, said bore having an axis (36), said furnace body (12) having lateral contact pieces (20, 22) with said contact surfaces (38, 40) arranged such that heating current passes through the furnace (10) substantially transverse to the axis (36) of the bore (14),
    (b) end faces (138, 140) of the tubular furnace body (12) form gaps (134, 136) with the inner wall of the cavity formed by the contacts (54, 56), and
    (c) means for guiding the inert gas flow comprise inert gas inlet ports (100, 102, 104, 106) in the area of the contact pieces (20, 22) such that the inert gas flows along the contact pieces (20, 22), around the tubular furnace body (12) and through the gaps (134, 136), into the ends of the bore (14) of the furnace body (12), and through the bore 14 to exhaust through the aligned sample inlet ports (116, 120).

27. The device of claim 26 wherein
    (a) the contact pieces (20, 22) of the furnace (10) have a generally cylindrical shape with opposite planar surfaces (28, 30) and are conically tapered at their ends in the area of the cylindrical outer surfaces (24, 26) in order to form the contact surfaces (38, 40),
    (b) the contacts (54, 56) have concave-conical contact surfaces (96, 98) complementary to the contact surfaces (38, 40) of the furnace (10), and
    (c) the contact surfaces (96, 98) of the contacts (54, 56) each surround one inert gas passage (78, 94), respectively, which are adapted for the supply of inert gas, said inert gas inlet ports (100, 102, 104, 106) being formed between the contact surfaces (96, 98) of the contacts (54, 56) and the planar surface (28, 30) of the contact pieces (20, 22) of the furnace (10).

28. The device of claim 27 wherein the sample inlet port (120) provided in one contact (54) is formed by the bore of a chimney (122) inserted into the contact (54) having an end face which forms an annular gap (132) with the planar surface (130) of the furnace (10).

29. The device of claim 28 wherein the chimney (122) with an outer thread (124) is screwed into a threaded bore (126) of the contact (54) and is vertically adjustable by rotation.

* * * * *